United States Patent
Vidlund et al.

(12) 
(10) Patent No.: US 10,765,511 B2
(45) Date of Patent: *Sep. 8, 2020

(54) TRANSCATHETER HEART VALVE WITH PLICATION TISSUE ANCHORS

(71) Applicant: VDYNE, LLC, Dallas, TX (US)

(72) Inventors: Robert Vidlund, Forest Lake, MN (US); Mark Christianson, Maple Grove, MN (US); David Holtan, Maple Grove, MN (US)

(73) Assignee: VDYNE, INC., Maple Grove, MN (US)

( * ) Notice: Subject to any disclaimer, the term of this patent is extended or adjusted under 35 U.S.C. 154(b) by 250 days.

This patent is subject to a terminal disclaimer.

(21) Appl. No.: 16/016,512

(22) Filed: Jun. 22, 2018

(65) Prior Publication Data

US 2019/0388218 A1    Dec. 26, 2019

(51) Int. Cl.
*A61F 2/24*    (2006.01)

(52) U.S. Cl.
CPC .......... *A61F 2/2409* (2013.01); *A61F 2/2418* (2013.01); *A61F 2/2427* (2013.01); *A61F 2220/0008* (2013.01); *A61F 2250/0004* (2013.01); *A61F 2250/0069* (2013.01)

(58) Field of Classification Search
CPC ........ A61F 2/24; A61F 2/2412; A61F 2/2427; A61F 2/2466
See application file for complete search history.

(56) References Cited

U.S. PATENT DOCUMENTS

2014/0222136 A1* 8/2014 Geist ..................... A61F 2/2436
623/2.11

\* cited by examiner

*Primary Examiner* — Gregory A Anderson
(74) *Attorney, Agent, or Firm* — Juneau & Mitchell; Todd L. Juneau (57) ABSTRACT

The invention relates to a transcatheter heart valve replacement (A61F2/2412), and in particular a device and method for percutaneous annular plication and heart valve deployment for mounting a pressure actuated flow control sleeve, a pinch valve, as a replacement device for a heart valve, whereby the prosthesis has an atrial annular flange or cuff having one or more integral plication tissue anchors for engaging the valve annulus, wherein the is a reciprocating mechanical member that is compressed by pressurized working fluid within the heart during ventricular systole.

13 Claims, 5 Drawing Sheets

TRANSCATHETER HEART VALVE WITH PLICATION TISSUE ANCHORS

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to a transcatheter heart valve replacement (A61F2/2412), and in particular a device and method for percutaneous annular plication and heart valve deployment for mounting a pressure actuated flow control sleeve, a pinch valve, as a replacement device for a heart valve, whereby the prosthesis has an atrial annular flange or cuff having one or more integral plication tissue anchors for engaging annular tissue, wherein the is a reciprocating mechanical member that is compressed by pressurized working fluid within the heart during ventricular systole.

DESCRIPTION OF THE RELATED ART

The human heart has four chambers, two upper collection chambers are called atrium, and two lower pumping chambers called ventricles. The right-side atrium receives blood from the body and has a trapdoor opening, called a tricuspid valve, that delivers blood to the right-side ventricle. The right ventricle then pumps the blood a short distance, through a one-way valve called a pulmonary valve, to the lungs where the blood is oxygenated. When the oxygenated blood is returned to the left side of the heart from the lungs, the blood reaches the left upper, collection chamber, called the left atrium. Here, the blood is released through a second trapdoor opening, called a mitral valve, into the large, muscular left ventricle, which pumps the blood at high pressure through a one-way valve called an aortic valve to return the oxygenated blood back to the body.

Heart valve disease, such as those caused by damage or a defect, can include stenosis and valvular insufficiency or regurgitation. Valvular stenosis causes the valve to become narrowed and hardened which can prevent blood flow to a downstream heart chamber or structure (e.g., aorta) to occur at the proper flow rate and cause the heart to work harder to pump the blood through the diseased valve. Diseased or damaged valves, which can be congenital, age-related, drug-induced, or caused by infection, can result in an enlarged, thickened heart that loses elasticity and efficiency.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle.

For example, the repair or replacement of a valve can present numerous challenges due to differing anatomies and etiologies presented by individual patients, including varying sizes and topologies associated with an abnormal or unhealthy aortic valve that prevents proper alignment of the replacement (e.g., prosthetic) valve which can cause leakage, valve impingement or dislodgement of the prosthesis. Additionally, stenosis of a valve can deform the valvular area which can result in paravalvular leakage around an implanted replacement valve. Additional challenges can include providing a prosthetic valve that can be adjusted or repositioned during or after implantation and/or for replacing a previously implanted prosthetic valve.

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting disc technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The invention provides numerous advantages over prior designs. Specifically, the problems are addressed by providing a transcatheter delivered prosthetic valve having an asymmetric pericardial tissue covered wire frame with an upper angled collar of scalloped diamond-shapes forming an atrial flange, the atrial flange connected to a middle ring of longitudinally vertical diamond-shapes that is used to mount a reciprocating flow control conduit/tube, wherein the upper flange has a steep angle of inclination at the septal region, a shallower angle of inclination around the anterior and posterior annular regions, and an indent or cutout area near the coronary sinus region, wherein the septal region of the flange is contemplated as angled between 30-90 degrees to the horizontal plane of the annulus, and having a polyester material covering to promote tissue ingrowth, and a non-leaflet containing reciprocating tube disposed with a lumen of the wire frame to reduce stenosis and calcification, and a plurality of plication tissue anchors mounted on the wire frame for engaging annular tissue.

In some embodiments, there is a second lower angled collar of scalloped diamond shapes forming an sub-annular ventricular flange.

Accordingly, the present invention is directed to a transcatheter heart valve replacement comprising: an atrial sealing cuff frame, said cuff frame connected to a collapsible flow control sleeve that provides a reciprocating closable channel from a heart atrium to a heart ventricle, said cuff frame comprised of a braided or laser-cut wire frame having a substantially circular central aperture, said cuff frame partially covered with a biocompatible material, said collapsible flow control sleeve connected at an upper end to an inner perimeter of the central aperture of the cuff frame, and the collapsible flow control sleeve extending beyond the central aperture of the cuff frame and having a lower end positioned with the ventricle of the heart, and a plurality of plication tissue anchors, each mounted on the cuff frame for engaging annular tissue.

In another preferred embodiment, the invention comprises a transcatheter heart valve replacement as described and claimed herein, wherein the plication tissue anchor comprises a floating radio-opaque marker threaded onto the plication tissue anchor, wherein advancing the plication tissue anchor through tissue moves the floating radio-opaque marker from an initial distal lower thread position on the anchor to a secondary position on a higher thread.

In another preferred embodiment, the invention comprises a transcatheter heart valve replacement as described and claimed herein, wherein one or more of the plication tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

In another preferred embodiment, the invention comprises a transcatheter heart valve replacement as described and claimed herein, wherein the cuff frame is configured as a flat cone shape having a diameter R of 50-70 mm, a diameter r of 20-30 mm, and a height of 20-40 mm.

In another preferred embodiment, the invention comprises a transcatheter heart valve replacement as described and claimed herein, wherein the cuff frame has an inner wall and an outer wall, said inner wall having a biocompatible material comprising pericardial tissue, and said outer wall having a biocompatible material comprising a woven synthetic polyester material.

In another preferred embodiment, the invention comprises a transcatheter heart valve replacement as described and claimed herein, wherein the cuff frame is configured as an hourglass flat conical shape having a top diameter R1 of 50-70 mm, a bottom diameter R2 of 50-70 mm, an internal diameter r of 20-30 mm, and a height of 20-50 mm.

In another preferred embodiment, the invention comprises a transcatheter heart valve replacement as described and claimed herein, wherein the collapsible flow control sleeve has an internal diameter of 20-30 mm and a height of 30-80 mm, said sleeve comprising three substantially flat rectangular panels of pericardial material joined to form a rounded triangular cylinder.

In another preferred embodiment, the invention comprises a transcatheter heart valve replacement as described and claimed herein, wherein the transcatheter heart valve replacement is compressible and fits when compressed within the internal diameter of a transcatheter implantation catheter having an internal diameter less than 22 Fr (7.33 mm) to 34 Fr (9.33 mm).

In another preferred embodiment, the invention comprises a transcatheter heart valve replacement as described and claimed herein, wherein the collapsible flow control sleeve is supported with one or more longitudinal supports integrated into a fabric or material of the collapsible flow control sleeve, the one or more longitudinal supports selected from rigid or semi-rigid ribs, rigid or semi-rigid battons, rigid or semi-rigid panels, and combination thereof.

In another preferred embodiment, the invention comprises a transcatheter heart valve replacement as described and claimed herein, wherein one or more of the plication tissue anchors or secondary tissue anchors are selected from the group consisting of: a helical coil, a screw, a dart, a pin, and a fastener means.

In another preferred embodiment, the invention comprises a method for securing a transcatheter heart valve prosthesis within a heart, the method comprising the steps: (i) advancing a procedure guide wire into a ventricle of a heart; (ii) advancing a 22 Fr-34 Fr steerable catheter over the procedure guide wire to deliver a compressed transcatheter heart valve prosthesis described herein to an atrium of the ventricle of the heart; (iii) advancing the catheter to the valve annulus and releasing the self-expanding atrial sealing collar from within the catheter; (iv) advancing a plication dome over a dome guide wire to a plication window of the cuff frame; (v) anchoring a plication tissue anchor through the plication and into the annular tissue; and (vi) releasing said dome guide wire from attachment to the plication dome by actuating a release mechanism, and withdrawing the dome guide wire and steerable catheter from the heart.

BRIEF DESCRIPTION OF THE SEVERAL VIEWS OF DRAWING

FIG. 1 shows a a pair of tissue anchors accessing annular tissue through the biocompatible material covering the valve frame.

FIG. 2 shows a pair of tissue anchors accessing annular tissue through the biocompatible material covering the valve frame.

FIG. 3 shows a pair of tissue anchors accessing annular tissue through the biocompatible material covering the valve frame.

FIG. 4 shows polyester mesh covering a valve frame encircling a collapsible flow control sleeve.

FIG. 6 shows a valve prosthesis with a valve frame having an atrial cuff and 3 topologically diverse tissue anchors mounting the heart valve prosthesis to the annular tissue.

FIG. 7 shows a valve prosthesis with a valve frame having an atrial cuff and a ventricular cuff and 3 topologically diverse tissue anchors mounting the heart valve prosthesis, 2 tissue anchors mounting directly to the annular tissue, and 1 tissue anchor connecting the atrial cuff to the ventricular cuff and optionally further connecting to the sub-annular tissue below the ventricular cuff.

FIG. 8 shows a valve prosthesis with a valve frame having an atrial cuff and a ventricular cuff with multiple tissue anchors in a pre-attachment position before the tissue anchors are secured to annular tissue.

FIG. 9 shows a valve prosthesis with a valve frame having an atrial cuff and a ventricular cuff with multiple tissue anchors in a post-securement position after the tissue anchors have been secured to annular tissue.

FIG. 10(a) shows the tissue anchor accessing the annular tissue with the radio-opaque marker at the distal end of the anchor and in contact with the atrial surface of the annular tissue. FIG. 10(b) shows the tissue anchor advancing into the annular tissue with the radio-opaque marker threaded onto the tissue anchor and maintaining position on the atrial surface of the annular tissue. FIG. 10(c) shows the tissue anchor completely advanced into the annular tissue such that the tissue anchor and the threaded floating marker are now adjacent, indicating the desired depth, tension, and/or plication of the tissue anchor with respect to the annular tissue.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid.

Wire Frame or Flange or Collar

In the description and claims herein, the terms "frame" or "flange or "collar" refers to flange, disk, band, ring, hem, rim, or belt that is a substantially flat cone shaped braided or laser-cut wire frame covered with a biocompatible material and having a central aperture. An atrial frame or collar is located in the atrium on the atrial floor and is used to direct blood into the sleeve attached to the aperture and seal against blood leakage around the sleeve. A ventricular frame or collar is located in the ventricle immediately below the native annulus and is used to prevent regurgitant leakage during systole, to prevent dislodging of the device during systole, to sandwich or compress the native annulus or adjacent tissue against the atrial collar, and to attach to a mid-section of the sleeve/conduit. The frames may be formed from braided or laser-cut Nitinol and as such may be compressed for transcatheter delivery and may be expandable as a self-expandable shape memory element or using a transcatheter expansion balloon. Some embodiments may have both an atrial collar and a ventricular collar, whereas other embodiments within the scope of the invention include prosthetic valves having either a single atrial collar or a single ventricular collar.

Sleeve

In the description and claims herein, the term "collapsible flow control sleeve" refers to a tube or conduit of flexible material that is open to blood flowing during diastole from atrium to ventricle, and that closes from systolic ventricular pressure applied to the outer surface. Repeated opening and closing in sequence can be described as "reciprocating". The tube is form of pinch valve, but is not a valve in the tradition sense having no internal leaflets.

Tissue Anchor

In the description and claims herein, the term "tissue anchor" or "plicationtissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of -, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles) As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Septomarginal Trabecula aka Moderator Band

The septomarginal trabecula of the right ventricle, originally termed the moderator band because it was thought to limit the lateral expansion of the chamber, is a muscular thickening extending from the interventricular septum to the base of the anterior papillary muscle. One of the main functions of the septomarginal trabecula is to convey the right branch of the atrioventricular bundle of the conducting system. The septomarginal trabecula also functions to form the anteroinferior border between the superior, smooth outflow tract of the ventricle and the trabeculated inflow tract. At its septal attachment, it may be continuous with the supraventricular crest.

Frame Structure

Preferably, the frame is made from superelastic metal wire, such as Nitinol™ wire or other similarly functioning material. The material may be used for the frame/stent, for the collar, and/or for anchors. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers. It is contemplated that the frame may be constructed as a braided wire frame or as a laser cut wire frame. Such materials are available from any number of commercial manufacturers, such as Pulse Systems. Laser cut wire frames are preferably made from Nickel-Titanium (Nitinol™), but also without limitation made from stainless steel, cobalt chromium, titanium, and other functionally equivalent metals and alloys, or Pulse Systems braided frame that is shape—set by heat treating on a fixture or mandrel.

One key aspect of the frame design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austhenitic, martensitic or super elastic. Martensitic and super elastic alloys can be processed to demonstrate the required compression features.

Laser Cut

One possible construction of the wire frame envisions the laser cutting of a thin, isodiametric Nitinol tube. The laser cuts form regular cutouts in the thin Nitinol tube.

Secondarily the tube is placed on a mold of the desired shape, heated to the Martensitic temperature and quenched. The treatment of the wire frame in this manner will form a device that has shape memory properties and will readily revert to the memory shape at the calibrated temperature.

Braided Wire

A frame can be constructed utilizing simple braiding techniques. Using a Nitinol wire—for example a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Tethers—The tethers are made from surgical-grade materials such as biocompatible polymer suture material. Non-limiting examples of such material include ultra high-molecular weight polyethylene (UHMWPE), 2-0 exPFTE (polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, where a prosthetic valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene—glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.l.) using 316L stainless steel wire frame as base for the drug Tacrolimus and utilizing integrated turbostratic carbofilm as the drug carrier. VESTA sync (MIV Therapeutics) using GenX stainless steel (316L) as base utilizing microporous hydroxyapatite coating as carrier for the drug Sirolimus. YUKON choice (Translumina) used 316L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316L stainless steel coated with polyethylene vinyl acetate (PEVA) and poly-butyl methacrylate (PBMA) for carrying the drug Sirolimus. Taxus (Boston Scientific) utilizes 316L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example

One preferred embodiment of a tethered transcatheter pinch valve is a heart valve substitute or successor comprising a pliant tubular conduit that is mounted on a resilient annular or ventricular frame, wherein the pliant tubular conduit is a reciprocating mechanical member that is compressed by pressurized working fluid, blood, within the ventricle during systole, and wherein the frame includes plication tissue anchors for capturing and anchoring annular tissue with tissue anchors. Importantly, this heart valve substitute has no leaflets and does not have a traditional valve configuration. Additionally, the device can be delivered to the ventricle compressed within a catheter, and expelled from the catheter to be deployed without open heart surgery.

Example

In another preferred embodiment of a transcatheter valve, comprises: (i) a atrial sealing frame and wherein the atrial frame includes plication tissue anchors for capturing and anchoring annular tissue with tissue anchors, and (ii) a ventricular sealing collar/flange/frame, each of said atrial and ventricular frame connected to (iii) a collapsible flow control sleeve that provides a reciprocating closable channel from a heart atrium to a heart ventricle, each of said frames comprised of a pair of flat conical shaped braided or laser-cut wire frame covered with a biocompatible material and each having a central aperture, the collapsible flow control sleeve connected at an upper end to an inner perimeter of the central aperture of the atrial sealing frame, the collapsible flow control sleeve connected at a middle section to an inner perimeter of the central aperture of the ventricular sealing frame, and the collapsible flow control sleeve extending beyond the central aperture of the ventricular sealing frame and having a lower end positioned with the ventricle of the heart, and (iv) from 2-12 tissue anchors, wherein the collapsible flow control sleeve defines a channel therein, said channel having a volume that ranges from 1.57 mL-18.84 mL, said sleeve having an average radius of 4.0-16.5 mm and an average height of 20-60 mm, said sleeve comprised of decellularized pericardium or polymer, said sleeve having top end, a bottom end, an internal surface, and an external surface, said sleeve is compressible under a pressure of 50-160 mm Hg on the external surface to close the channel, and said sleeve is expandable under a pressure of 40-80 mm Hg on the internal surface to open the channel, the collars have an average side length of 5-20 mm, an aperture having an average expanded diameter of 30-35 mm, and a perimeter having an average expanded diameter/circumference of 40-60 mm, said collars having a cover; and optional one-piece rigid or semi-rigid axial post disposed with the lumen of the sleeve to support the length-wise integrity of the flexible sleeve.

Example

In another preferred embodiment of a transcatheter valve, there is provided a feature wherein the sleeve is shaped as a conic cylinder, said top end having a diameter of 30-35 mm and said bottom end having a diameter of 8-20 mm.

Example

In another preferred embodiment of a transcatheter valve, there is provided a feature wherein the cover is comprised of polyester, polyethylene terephthalate, decellularized pericardium, or a layered combination thereof.

Example

In another preferred embodiment of a transcatheter valve, there is provided a feature wherein the nitinol frame supports a gel ring, wherein the gel ring is comprised of an expandable material enclosed within an outer sealing membrane, wherein the expandable material is a swellable powder within a polymeric matrix, a swellable polymeric matrix, or a swellable polymeric liquid.

Example

In another preferred embodiment of a transcatheter valve, there is provided a feature wherein the nitinol frame supports a deflatable ring, wherein the deflatable ring is comprised of a toroid-shaped sealed compartment having a valve, said sealed compartment fillable with a biocompatible liquid or gas, wherein upon removal of some or all of the biocompatible liquid or gas, the deflatable ring has a reduced diameter, and wherein upon removal of some or all of the biocompatible liquid or gas, the top spacer segment of the cylinder has a reduced height and the collar is compressed in the direction of the top wire frame.

Example

In another preferred embodiment of a transcatheter valve, there is provided a feature wherein the sleeve has an hourglass (hyperboloid) shape from top end to bottom end.

Example

In another preferred embodiment of a transcatheter valve, there is provided a feature wherein the bottom end of the sleeve has a sinusoidal edge, and wherein one or more sections of the sleeve edge may be secured to one or more rigid support posts.

Example

In another preferred embodiment of a transcatheter valve, there is provided a feature wherein the atrial frame comprises a threaded structure, wherein the threaded structure allows for a simple circular screw-type deployment of the device into a native annulus to aid in sealing and sizing of the top collar into the native annulus.

Example

In a preferred embodiment of the invention, there is also provided a method of controlling flow of bodily fluid within an enclosed cavity of a human body, said enclosed cavity having a reciprocating pressure differential, the method comprising the steps: (i) delivering the transcatheter prosthetic medical device described herein, to the enclosed cavity within the human body; (ii) arranging the prosthetic medical device whereby the sleeve and sleeve channel are arranged parallel to a flow of fluid entering the enclosed cavity; (iii) expanding a top frame above an entrance to the enclosed cavity to mount the top end of the sleeve within the entrance, whereby the top flange applies an compression force and seals the entrance, and expanding the bottom frame below the entrance to the enclosed cavity to position the bottom end of the sleeve within the enclosed cavity; wherein bodily fluid arriving at the enclosed cavity is diverted into the channel of the sleeve; wherein the reciprocating pressure differential comprises a low pressure state and a high pressure state; wherein bodily fluid flows into the channel to the enclosed cavity during the low pressure state, and wherein bodily fluid is prevented from flowing into the channel to the enclosed cavity during the high pressure state, wherein the high pressure state exerts a force on the external surface of the sleeve and reversibly collapses the channel.

Example

The transcatheter prosthetic heart valve may be percutaneously delivered using a transcatheter process via the carotid, but both carotid, femoral, sub-xyphoid, and intercostal access across the chest wall. The device is delivered via catheter to the right or left atrium and is expanded from a compressed shape that fits with the internal diameter of the catheter lumen. The compressed pinch valve is loaded external to the patient into the delivery catheter, and is then pushed out of the catheter when the capsule arrives to the atrium. The cardiac treatment technician visualizes this delivery using available imaging techniques such as fluoroscopy or ultrasound, and in a preferred embodiment the pinch valve self-expands upon release from the catheter since it is constructed in part from shape-memory material, such as Nitinol®, a nickel-titanium alloy used in biomedical implants.

In another embodiment, the pinch valve may be constructed of materials that requires balloon-expansion after the capsule has been ejected from the catheter into the atrium.

Once the atrial collar/frame and the conduit sleeve are expanded to their functional diameter, they is deployed into the native annulus. The optional ventricular collar is expanded below the annulus forming an layered stack with the collars on top and bottom and the native annulus in the middle. It is also contemplated that an optional support post may be deployed within the lumen or within the seam, of the sleeve. Once the frame is deployed about the tricuspid annulus, fasteners secure the device about the native annulus. Additional fastening of the device to a moderator band mounting may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

DRAWINGS

Figure 1:
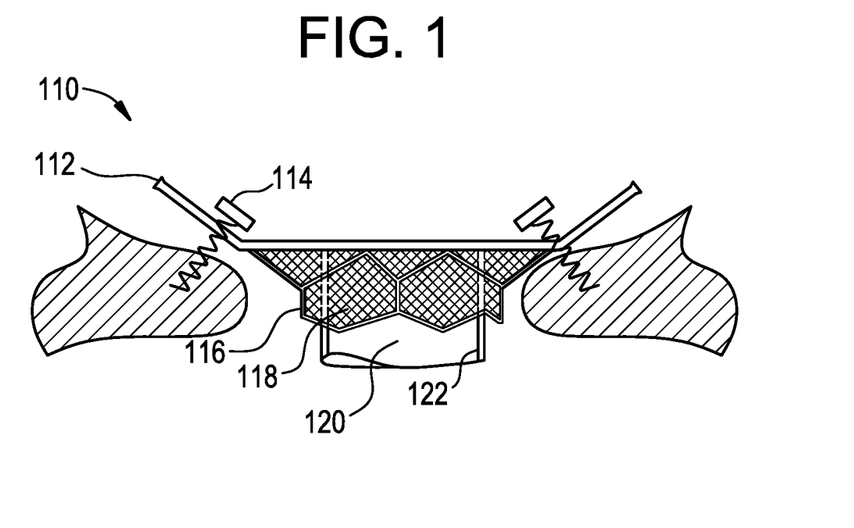
FIG. 1 is an illustration of a plan view of a heart valve prosthesis according to the present invention with a valve frame having an atrial cuff component.

Referring now to the drawings, FIG. 1 is an illustration of a plan view of a heart valve prosthesis 110 according to the present invention with a valve frame 116 having an atrial cuff component 112. FIG. 1 shows a pair of tissue anchors 114 accessing annular tissue through the biocompatible material 118 covering the valve frame 116. FIG. 1 also shows reciprocating flow control sleeve 120 supported by rigid support member 122. The wire frame 116 is preferably an open cell structure with substantially vertical diamond shaped cells creating a collar or cylinder, which has flared horizontal or angled diamond shaped cells forming the atrial cuff or flange component.

Figure 2:
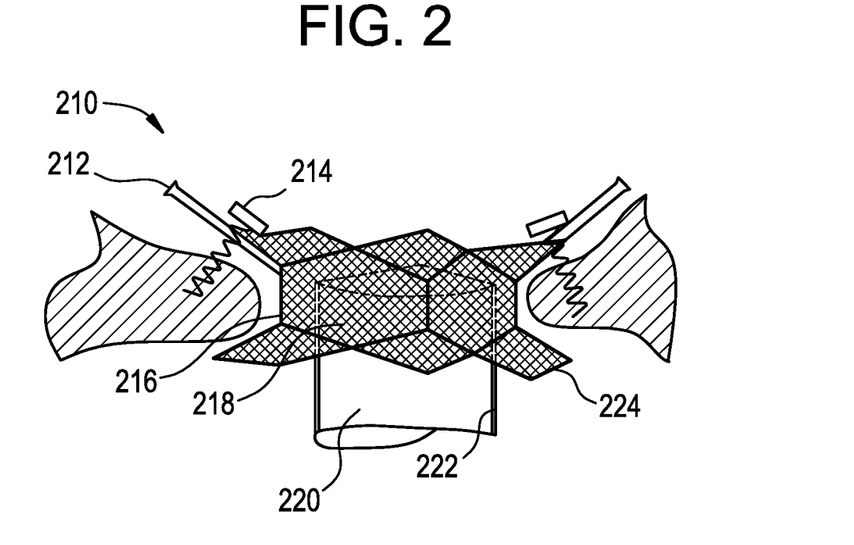
FIG. 2 is an illustration of a plan view of a heart valve prosthesis having according to the present invention with a valve frame having an atrial cuff component and a ventricular cuff component.

FIG. 2 is an illustration of a plan view of a heart valve prosthesis 210 having according to the present invention with a valve frame 216 having an atrial cuff component 212 and a ventricular cuff component 224. FIG. 2 shows a pair of tissue anchors 214 accessing annular tissue through the biocompatible material 218 covering the valve frame FIG. 2 also shows reciprocating flow control sleeve 220 supported by rigid support member(s) 222. The wire frame 216 is preferably an open cell structure with substantially vertical diamond shaped cells creating a collar or cylinder, which has flared horizontal or angled diamond shaped cells forming the atrial cuff or flange component 212, and flared angled diamond shaped cells forming the ventricular cuff or flange component 224. It is contemplated that atrial flange 212 is deployed supra-annularly and ventricular flange 224 is deployed sub-annularly.

Figure 3:
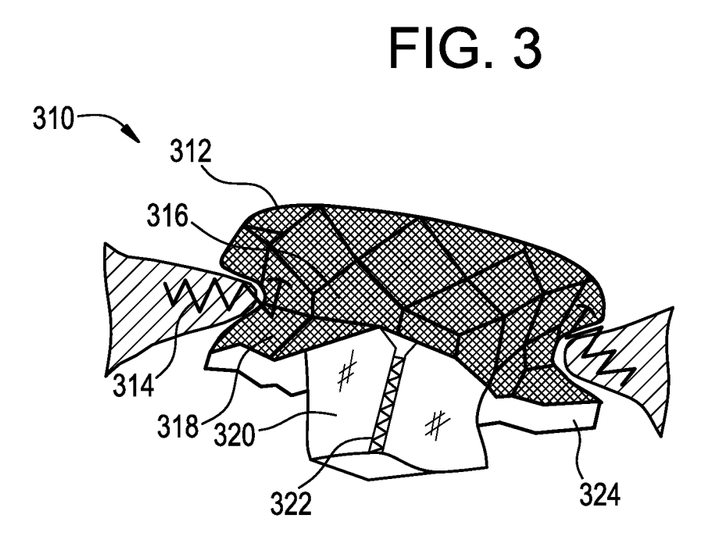
FIG. 3 is an illustration of a bottom perspective view of a heart valve prosthesis having according to the present invention with a valve frame having an atrial cuff component and a ventricular cuff component.

FIG. 3 is an illustration of a bottom perspective view of a heart valve prosthesis 310 having according to the present invention with a valve frame 316 having an atrial cuff component 312 and a ventricular cuff component 324. FIG. 3 shows a pair of tissue anchors 314 accessing annular tissue through the biocompatible material 318 covering the valve frame. FIG. 3 also shows reciprocating flow control sleeve 320 supported by rigid support member(s) 322. The wire frame 316 is preferably an open cell structure with substantially vertical diamond shaped cells creating a collar or cylinder, which has flared horizontal or angled diamond shaped cells forming the atrial cuff or flange component 312, and flared angled diamond shaped cells forming the ventricular cuff or flange component 324. It is contemplated that atrial flange 312 is deployed supra-annularly and ventricular flange 324 is deployed sub-annularly.

Figure 4:
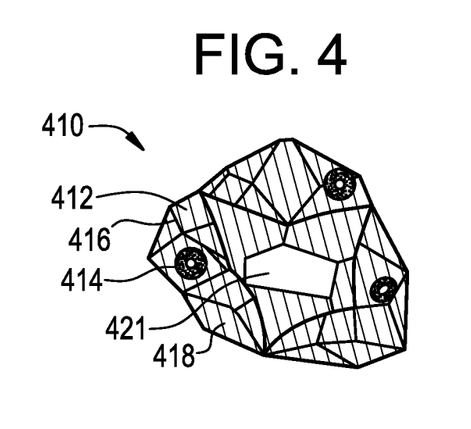
FIG. 4 is an illustration of a top view of a heart valve prosthesis according to the present invention.

FIG. 4 is an illustration of a top view of a heart valve prosthesis 410 according to the present invention. FIG. 4 shows polyester mesh 418 covering a valve frame 416 encircling a collapsible flow control sleeve 421. Atrial cuff component 412 and tissue anchors 414 are shown, and tissue anchor 414 is accessing annular tissue through the biocompatible material 418 covering the valve frame 416. The wire frame 416 is preferably an open cell structure with substantially vertical diamond shaped cells creating a collar or cylinder, which has flared horizontal or angled diamond shaped cells forming the atrial cuff or flange component 412. It is contemplated that atrial flange 412 is deployed supra-annularly.

Figure 5:
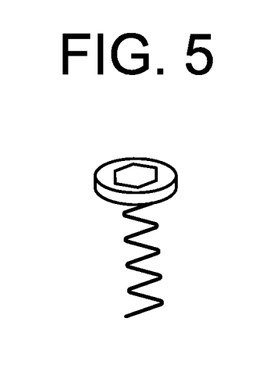
FIG. 5 is an illustration of a plan view of a tissue anchor having a straight thread and a constant pitch.

FIG. 5 is an illustration of a plan view of a tissue anchor having a straight thread and a constant pitch.

Figure 6:
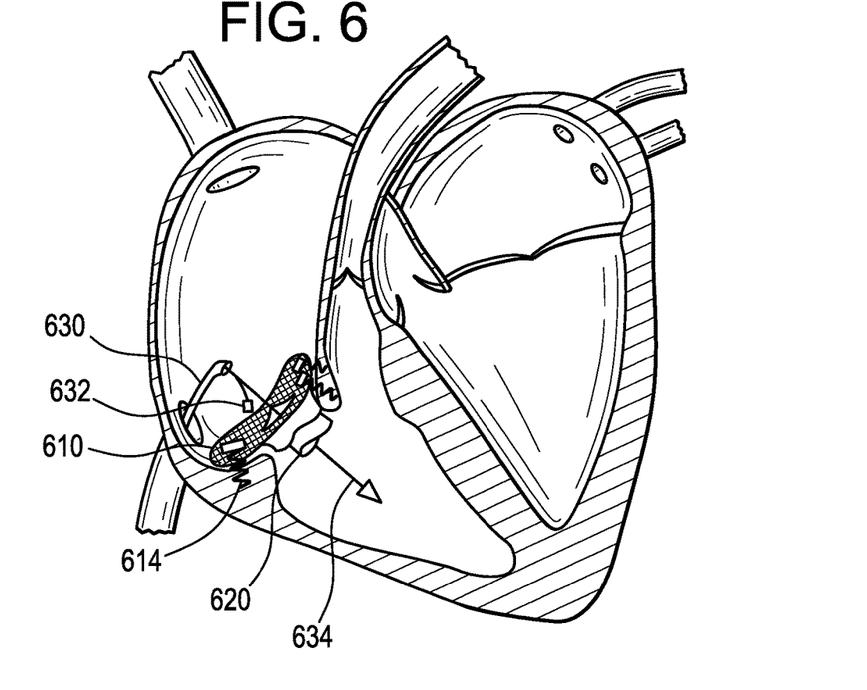
FIG. 6 is an illustration of a perspective view of a heart valve prosthesis according to the present invention deployed within the tricuspid annulus.

FIG. 6 is an illustration of a perspective view of a heart valve prosthesis 610 according to the present invention deployed within the tricuspid annulus. FIG. 6 shows a valve prosthesis 610 with a valve frame having an atrial cuff and 3 topologically diverse tissue anchors 614 mounting the heart valve prosthesis to the annular tissue. FIG. 6 shows catheter 630 and guidewire 634 extending down the axis of the lumen of the valve. Wire actuated tissue anchor tool 632 is used to tighten the tissue anchor 614 into the annular tissue. Reciprocating sleeve 620 is shown extending into ventricle and mounted from the distal portion of the valve 610.

Figure 7:
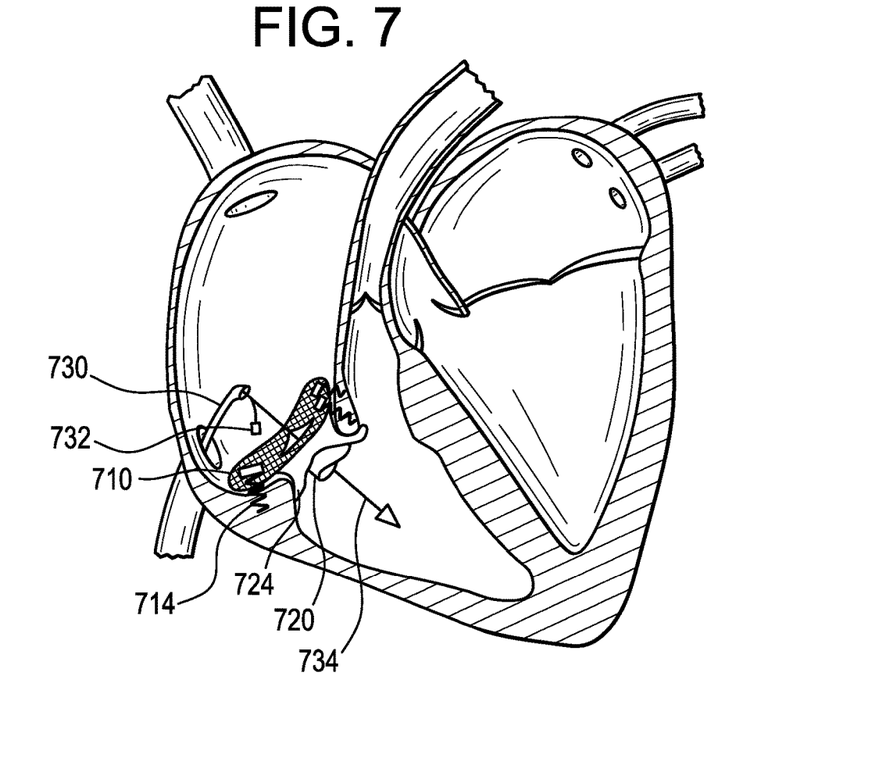
FIG. 7 is an illustration of a perspective view of a heart valve prosthesis according to the present invention deployed within the tricuspid annulus.

FIG. 7 is an illustration of a perspective view of a heart valve prosthesis 710 according to the present invention deployed within the tricuspid annulus. FIG. 7 shows a valve prosthesis with a valve frame having an atrial cuff and a ventricular cuff and 3 topologically diverse tissue anchors mounting the heart valve prosthesis, 2 tissue anchors mounting directly to the annular tissue, and 1 tissue anchor connecting the atrial cuff to the ventricular cuff and optionally further connecting to the sub-annular tissue below the ventricular cuff. FIG. 7 shows a valve prosthesis 710 with a valve frame having an atrial cuff and 3 topologically diverse tissue anchors 714 mounting the heart valve prosthesis to the annular tissue. FIG. 7 shows catheter 730 and guidewire 734 extending down the axis of the lumen of the valve. Wire actuated tissue anchor tool 732 is used to tighten the tissue anchor 714 into the annular tissue. Reciprocating sleeve 720 is shown extending into ventricle and mounted from the distal portion of the valve 710.

Figure 8:
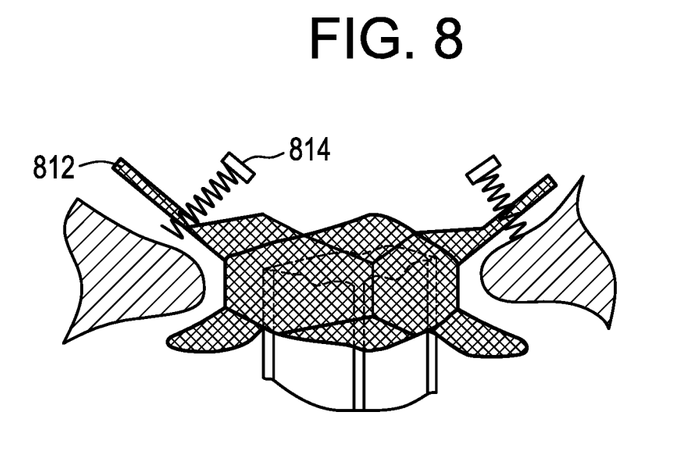
FIG. 8 is an illustration of a plan view of a heart valve prosthesis according to the present invention deployed within the tricuspid annulus.

FIG. 8 is an illustration of a plan view of a heart valve prosthesis according to the present invention deployed within the tricuspid annulus. FIG. 8 shows a valve prosthesis with a valve frame having an atrial cuff 812 and a ventricular cuff with multiple tissue anchors 814 in a pre-attachment position before the tissue anchors are secured to annular tissue.

Figure 9:
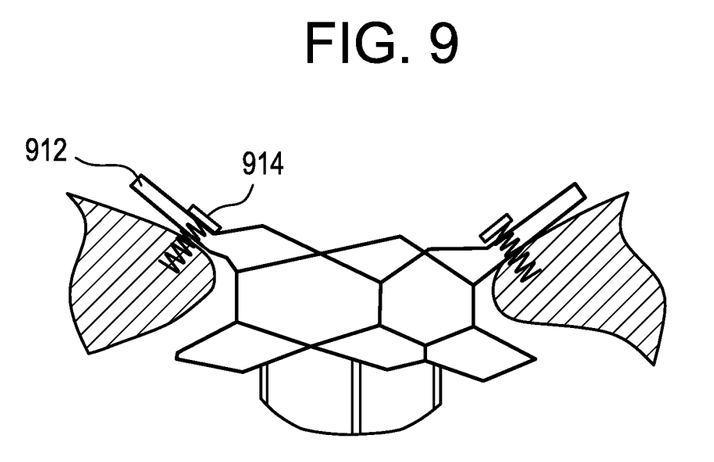
FIG. 9 is an illustration of a plan view of a heart valve prosthesis according to the present invention deployed within the tricuspid annulus.

FIG. 9 is an illustration of a plan view of a heart valve prosthesis according to the present invention deployed within the tricuspid annulus. FIG. 9 shows a valve prosthesis with a valve frame having an atrial cuff 912 and a ventricular cuff with multiple tissue anchors 914 in a post-securement position after the tissue anchors have been secured to annular tissue.

Figure 10A:
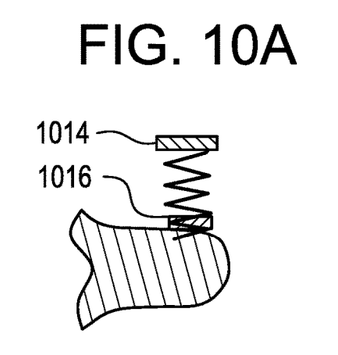
FIG. 10(a)-(c) is an illustration of a plan view of a tissue anchor having a floating radio-opaque marker.
Figure 10B:
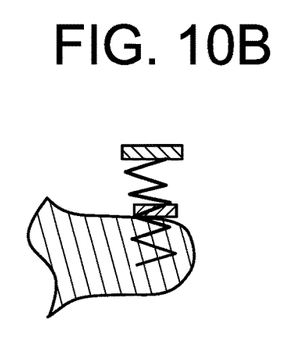
Figure 10C:
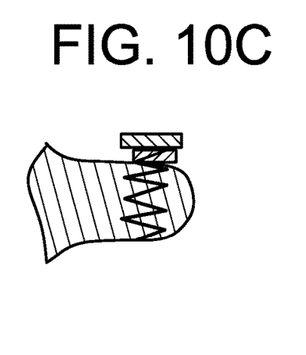

FIG. 10(a)-(c) is an illustration of a plan view of a tissue anchor 1014 having a floating radio-opaque marker 1016. FIG. 10(a) shows the tissue anchor 1014 accessing the annular tissue with the radio-opaque marker 1016 at the distal end of the anchor and in contact with the atrial surface of the annular tissue. FIG. 10(b) shows the tissue anchor 1014 advancing into the annular tissue with the radio-opaque marker 1016 threaded onto the tissue anchor and maintaining position on the atrial surface of the annular tissue. FIG. 10(c) shows the tissue anchor 1014 completely advanced into the annular tissue such that the tissue anchor and the threaded floating marker 1016 are now adjacent, indicating the desired depth, tension, and/or plication of the tissue anchor with respect to the annular tissue.

Figure 11:
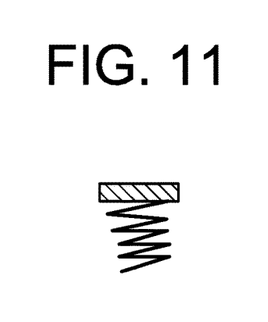
FIG. 11 is an illustration of a plan view of a tissue anchor having a straight thread and a constant pitch.

FIG. 11 is an illustration of a plan view of a tissue anchor having a straight thread and a constant pitch.

Figure 12:
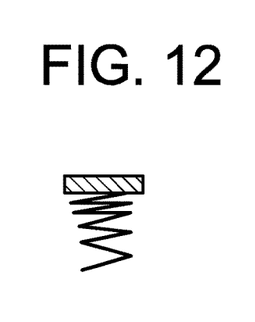
FIG. 12 is an illustration of a plan view of a tissue anchor having a straight thread and a variable pitch.

FIG. 12 is an illustration of a plan view of a tissue anchor having a straight thread and a variable pitch.

Figure 13:
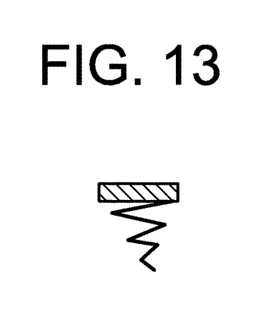
FIG. 13 is an illustration of a plan view of a tissue anchor having a tapered thread and a constant pitch.

FIG. 13 is an illustration of a plan view of a tissue anchor having a tapered thread and a constant pitch.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings.

It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A transcatheter heart valve replacement comprising:
   an asymmetric wire frame with an upper angled collar of scalloped diamond-shape cells forming an atrial flange;
   a middle ring defining a lumen connected to the atrial flange, the middle ring comprised of a plurality of diamond-shape cells;
   a reciprocating flow control member mounted on the middle ring and disposed within the lumen; and
   a plurality of tissue anchors, each tissue anchor mounted on the wire frame for engaging annular tissue;
   wherein the atrial flange has a steep angle of inclination at a septal region of the wire frame, and a shallower angle of inclination around anterior and posterior annular regions of the wire frame;
   wherein the wire frame has an inner covering of pericardial tissue, and an outer covering of a polyester material.

2. The transcatheter heart valve replacement of claim 1, wherein there is a second lower angled collar of scalloped diamond shapes forming a sub-annular ventricular flange.

3. The transcatheter heart valve replacement of claim 1, wherein the steep angle is between 30-90 degrees to the horizontal plane of the annulus.

4. The transcatheter heart valve replacement of claim 1, wherein the tissue anchor comprises a floating radio-opaque marker threaded onto the tissue anchor, wherein advancing the tissue anchor through tissue moves the floating radio-opaque marker from an initial distal lower thread position on the anchor to a secondary position on a higher thread.

5. The transcatheter heart valve replacement of claim 4, wherein one or more of the tissue anchors or the secondary tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

6. The transcatheter heart valve replacement of claim 4, wherein the cuff frame is configured as a flat cone shape having a diameter R of 50-70 mm, a diameter r of 20-30 mm, and a height of 20-40 mm.

7. The transcatheter heart valve replacement of claim 4, wherein the cuff frame has an inner wall and an outer wall, said inner wall having a biocompatible material comprising pericardial tissue, and said outer wall having a biocompatible material comprising a woven synthetic polyester material.

8. The transcatheter heart valve replacement of claim 4, wherein the cuff frame is configured as an hourglass flat conical shape having a top diameter R1 of 50-70 mm, a bottom diameter R2 of 50-70 mm, an internal diameter r of 20-30 mm, and a height of 20-50 mm.

9. The transcatheter heart valve replacement of claim 4, wherein the collapsible flow control member has an internal diameter of 20-30 mm and a height of 30-80 mm, said member comprising three substantially flat rectangular panels of pericardial material joined to form a rounded triangular cylinder.

10. The transcatheter heart valve replacement claim 4, wherein the transcatheter heart valve replacement is compressible and fits when compressed within the internal diameter of a transcatheter implantation catheter having an internal diameter less than 22 Fr (7.33 mm) to 34 Fr (9.33 mm).

11. The transcatheter heart valve replacement of claim 4, wherein the collapsible flow control member is supported with one or more longitudinal supports integrated into a fabric or material of the collapsible flow control member, the one or more longitudinal supports selected from rigid or semi-rigid ribs, rigid or semi-rigid battons, rigid or semi-rigid panels, and combination thereof.

12. The transcatheter heart valve replacement of claim 4, wherein one or more of the tissue anchors are selected from the group consisting of: a helical coil, a screw, a dart, a pin, and a fastener means.

13. A method for securing a transcatheter heart valve prosthesis within a heart, the method comprising the steps:
(i) advancing a procedure guide wire into a ventricle of a heart;
(ii) advancing a 22 Fr-34 Fr steerable catheter over the procedure guide wire to deliver a compressed transcatheter heart valve prosthesis of claim 1 to an atrium of the ventricle of the heart;
(iii) advancing the catheter to the valve annulus and releasing the self-expanding atrial sealing collar from within the catheter; and
(iv) advancing and anchoring a tissue anchor through the cuff wire frame and into the annular tissue.

\* \* \* \* \*